United States Patent [19]
Lebovitz

[11] Patent Number: 5,993,810
[45] Date of Patent: Nov. 30, 1999

[54] METHOD OF SOFTENING OR RIPENING THE CERVIX OF A FEMALE MAMMAL USING COLLAGENASE

[76] Inventor: Shamir Israel Lebovitz, 27 Emeck Habracha Street, Tel Aviv, Israel

[21] Appl. No.: 08/818,205

[22] Filed: Mar. 14, 1997

Related U.S. Application Data

[60] Provisional application No. 60/013,591, Mar. 15, 1996.

[51] Int. Cl.[6] ........................................... A61K 38/48
[52] U.S. Cl. .............................. 424/94.67; 415/2; 415/21
[58] Field of Search ............................. 424/94.67; 514/2, 514/21

[56] References Cited

U.S. PATENT DOCUMENTS

| | | | |
|---|---|---|---|
| 3,678,158 | 7/1972 | Sussman | 424/94.67 |
| 4,174,389 | 11/1979 | Cope | 424/94.67 |
| 4,338,300 | 7/1982 | Gelbard | 424/94.67 |

FOREIGN PATENT DOCUMENTS

| | | |
|---|---|---|
| 0 543 376 A1 | 5/1993 | European Pat. Off. . |
| 05209882 | 8/1993 | Japan . |

OTHER PUBLICATIONS

Coulam et al., Prostaglandins, Leukotrienes Essent. Fatty Acids 49(6): 959–961 (1993).
Gonzalez et al., Ginecologia Y Obstetricia De Mexico 62: 27–30 (Jan. 1994).
Ohno et al., European Journal of Endocrinology 130(5): 478–484 (May 1994).
Goshowaki et al., Protaglandins 36(1): 107–114 (1988).
Zicari et al., Journal of Reproductive Immunology 29: 197–208 (1995).
Chwalisz et al., Human Reproduction 9(11): 2173–7281 (1994). Abstract.
El Maradny et al., Eur. J. Obstet. Gynecol. Reprod. Biol. 60(1): 75–80 (1995). Abstract.
Ito et al., Biol. Reprod. 37(3): 511–517 (1987). Abstract.
Arck et al., American Journal of Reproductive Immunology 33(1): 74–80 (1995). Abstract.
Rajabi, M. R. et al "Elevated tissue levels of collangenase during dilation of uterine cervix in human parturation"; American Journal of Obstetrics and Gynecology, vol. 159, No. 4, pp. 971–976 (1988).
Osmers, R. et al "Collangenase activity in the cervix of non–pregnant and pregnant woman"; Archives of Gynecology and Obstetrics, vol. 248, No. 2, pp. 75–80 (1990).

*Primary Examiner*—Jean C. Witz
*Attorney, Agent, or Firm*—Roberts & Mercanti, L.L.P.

[57] ABSTRACT

The present invention relates to the use of collagenase and/or one more substances which stimulate the production of naturally occurring collagenase in the cervix to induce labor in a female mammal, and in particular a female human or to terminate pregnancy in such a female mammal. The substances which stimulate the production of naturally occurring collagenase include Interleukin 1 beta, Interleukin 2, Interleukin 6, Interleukin 8 and tumor necrosis factor.

22 Claims, No Drawings

METHOD OF SOFTENING OR RIPENING THE CERVIX OF A FEMALE MAMMAL USING COLLAGENASE

CROSS-REFERENCE TO RELATED APPLICATIONS

This application claims the benefit of priority from U.S. Provisional Patent Application No. 60/013,591 filed Mar. 15, 1996, the contents of which are incorporated herein by reference.

FIELD OF THE INVENTION

THIS INVENTION relates to a medicament for use in a method of treatment of female mammals, including humans.

SUMMARY OF THE INVENTION

According to a first aspect of the invention there is provided a medicament for use in a method of treatment of female mammals, including humans, for softening or ripening the cervix of the uterus, said medicament comprising a collagenase substance, and said method comprising administering an effective amount of said medicament.

The term "collagenase substance" as used herein is intended to include collagenase and/or one or more substances which stimulates the production of naturally occurring collagenase in the cervix.

The said medicament may contain at least one pharmaceutically acceptable excipient or carrier.

According to a second aspect of the invention there is provided a use of a collagenase substance in the preparation of a medicament for softening or ripening the uterine cervix of female mammals, including humans.

According to another aspect of the invention there is provided a method for softening or ripening the uterine cervix of female mammals, including humans, which method comprises administering an effective amount of collagenase substance.

The invention can beneficially be used, for example, in induction of labor, in termination of pregnancy, in various diagnostic procedures such as D & C and hysteroscopy or in operative hysteroscopy.

The collagenase used in this invention may be any collagenase having a molecular weight of approximately 40,000 daltons. It may be a human collagenase or a recombinant collagenase.

Collagen is a naturally occurring fibrous protein found in humans and animals. Collagen is one of the most abundant proteins in mammals and comprises various naturally occurring amino acids, e.g. glycine, alanine, proline and hydroxyproline. The uterine cervix contains collagen which is degraded by the collagenase enzyme, particularly collagen type I and collagen type III.

During labour and until the end of the delivery, the amount of collagen in the cervix is usually significantly reduced. The collagen in the cervix and lower segment of the cervix is degraded as a result of an increase in the amount of collagenase. The ratio of undissolved hydroxyproline in collagen to the total amount of protein in collagen generally is about 0.75 in women not in pregnancy. Such ratio is generally about 0.3 in women in active labor. This is an indication of the degree of degradation of collagen caused by collagenase in the lower segment of the cervix and the uterus in women in or nearing labor. Reduction in the amount of collagen results in a softening or ripening of the cervix, which allows dilation thereof and thereby facilitates birth.

Various methods can be employed to determine whether or not the cervix is in a "favorable condition". One such method is by means of measuring the Bishop score of the cervix of a woman in labour, e.g. to determine whether or not the cervix of a woman has reached a favorable condition of softness or ripeness prior to delivery. A Bishop score on a scale of 0–10 is carried out on the cervix. The parameters of the cervix measured to determine the Bishop score are set out hereunder:

Length of cervix—0–3 points

Dilation of cervix—0–3 points

Consistency of cervix—0–2 points

Position of cervix (anterior, mid and posterior)—0–2 points (i.e. posterior=0 —anterior=2)

Station of leading part (head breach)—0–3 points

A Bishop score >6 indicates that the cervix is in a "favorable condition" for dilation and a Bishop score <4 indicates that the cervix is in an "unfavorable condition".

However, on occasion induction of labor is required when the cervix is in an "unfavorable condition", i.e. the collagen content has not been reduced by natural biological processes of the pregnant female mammal body, and maintains the cervix in a firmer, unripened condition which does not readily allow dilation thereof.

Furthermore, access into and from the uterus is not necessarily limited to natural childbirth. For example, in various clinical situations, access into the uterus is required for purposes of curettage, while termination of pregnancy requires passage through the cervix of an embryo or fetus. It will be appreciated that in such cases, the cervix is unlikely to be in a favorable condition.

It will be appreciated that the extent to which dilation of the cervix is required for childbirth is greater than what generally is required for early termination of pregnancy or curettage. Thus, "effective amount" of collagenase or of the medicament should be understood as being sufficient to give the desired result which being non-toxic to the female mammal.

Furthermore, "softening or ripening" of the cervix should be understood as meaning such change in the collagen content of the cervix as will allow desired dilation thereof.

By stimulating, enhancing or increasing the collagenase activity or amount of collagenase in the cervix of pregnant females, according to the method of the present invention, the cervix can be softened or ripened when desired, e.g. prior to termination of pregnancy or induction of labor or various diagnostic procedures. In other words, the medicament can be administered to female mammals to provide at least some of the collagenase necessary to degrade collagen in the cervix and thereby ripen or soften said cervix. The collagenase administered may augment any naturally produced collagenase present in the cervix and/or stimulate the production of naturally occurring collagenase in the cervix or the release of prostaglandins.

The substances which stimulate the production of naturally occurring collagenase in the cervix would normally comprise one or more of Interleukin 1 beta, 2, 6 and 8 as well as tumor necrosis factor (TNF). Interleukin 1 beta, 2, 6 and 8 are readily obtainable. These substances, the various Interleukins as well as TNF, can be synthesised commercially using bioengineering. Interleukin 1 beta, 2, 6 and 8 and TNF cause the release of collagenase, elastase and gelatinase in the human with resulting ripening of the cervix. The medicant substance i.e. Interleukin 1 beta, 2, 6 or 8 or TNF may be inserted into the vagina or the cervix or may be applied in the amniotic fluid, extra-amniotically or into the cervical canal The substances can be conveniently applied as pharmaceutically acceptable tablets, gels or solutions in the range of about 100 micrograms (100 μg) to about 2 milligrams (2 mg) per gram of cervical tissue.

Naturally, routine experimentation can be used to optimize the effective amount of collagenase required to be used in a medicament in accordance with the invention. The medicament may be administered by injection into the cervix in such amount as will provide collagenase to the cervix at a concentration in the range of from about 10 to about 200 and preferably from about 10 to about 15 I.U. per gram cervical tissue or to increase the colleganse in the systemic circulation to 70 ng/ml.

The medicament may be administered in various forms and by various routes, e.g. subcutaneously, intramuscularly, intravenously, intracervically, etc., and therefore the medicament may be provided in the form of a liquid or a solid formulation e.g. pills, gels or capsules. The preferred method of administration of the medicament is by injection into a lip of the cervix as a pharmaceutically acceptable liquid, and preferably by injection into both lips of the cervix.

The particular pharmaceutical carrier used will vary, depending on the form of the medicament and the intended method of administration. Such carriers are well known to those of ordinary skill in the art and can be selected without undue experimentation.

The medicament and method according to the present invention may be administered in conjunction or in combination with other agents or methods which heretofore have been used in an endeavor to soften or ripen the cervix. These include the use of hydrophillic organic material obtained from seaweed i.e. *Laminaria japonicum;* synthetic hydrophillic material, e.g. such as that sold under the trademark Lamicel; prostaglandins in gel or tablet form; and intravenously administered oxytocin. Furthermore, collagenase may be used in combination with at least one other enzyme such as yaloronidase, elastase in heparin sulphatase, dermatin sulphatase or the like, the other enzyme(s) facilitating the degradation of mucopolysaccharides in the cervix and, the collagenase degrading the collagen.

Collagenase enzyme for use in the present invention is readily obtainable from commercial sources. It can also be synthesised commercially using the bacterium *Clostridium hystoliticum, E. coli* or by mammalian cells by genetics engineering.

DETAILED DESCRIPTION OF THE INVENTION

The invention is now described with reference to the following proposed non-limiting examples of a method of treatment of human female subjects using a medicament in accordance with the invention.

EXAMPLE 1

Termination of pregnancy in the first trimester

Fifty women undergoing curettage in the first trimester of pregnancy are recruited for the study. The study is a double blind randomized study with collagenase enzyme at a concentration of 10–200 I.U. per gram cervical tissue being administered to 25 of the women, and saline at a concentration of 0.9% by mass being administered to the remaining 25 women. 2 ml injection ampules are prepared by a pharmaceutical company so that neither the medical nor nursing staff nor the patient are able to identify whether or not the ampule contains saline or collagenase. The ampules are not marked with a code so that the person running or controlling the test is unable to identify which patients are given saline and which are given collagenase treatment (a double blind study).

Twelve hours before dilation and curettage, 2 ml of the collagenase or saline solution is injected at the anterior and posterior lip of the cervix, 1 ml being injected to each lip at the six and the twelve o'clock positions. Serum, prostaglandin $F_2\alpha$ (i.e. $pgF_2\alpha$) and $E\alpha$ (i.e. $pgE\alpha$) levels are measured before injecting the cervix and again before termination of pregnancy by using Amerlex-magnetic preparation obtainable from the Weil Organisation of South Africa. At the time of the curettage, the pressure required to insert Hegar dilation instruments sizes 6–12 is measured by the pressure measuring instrument used by N. D. Goldstuck according to Goldstuck N. D., Holloway—"Effects of Recent Childbirth and Lactation". 159–164, 1988. The duration of the induction or the delivery interval of labour as well as the estimated blood loss is recorded in each case.

EXAMPLE 2

Termination of pregnancy in the first trimester

Example 1 is repeated with the active substance administered so that the collagenase in the serum of the patients will be 70 ng/ml.

EXAMPLE 3

Termination of pregnancy in the second trimester

Fifty women undergoing termination of pregnancy in the second trimester are recruited for this study. The identical dosages of collagenase or saline is injected into the cervix as described in Example 1 above. The Bishop score is measured prior to injection and again after twelve hours and recorded. Routine termination of pregnancy is performed by injecting $pgE_2\alpha$ extra-amniotically. The interval between induction and delivery is then recorded.

EXAMPLE 4

Termination of pregnancy in the second trimester

Example 3 is repeated with the following modifications. After ripening of the cervix is noted, oxytocin is administered intreveneously. The oxytocin is in a saline solution comprising 5 units in 1000 ml and is supplied at 15 to 40 drops per minute.

EXAMPLE 5

Termination of pregnancy in the second trimester

Example 3 is repeated with the following modifications. The active substance is Interleukin 1-beta. The active substance is injected into the amniotic fluid. The dosage is 100 μg to 2 mg per gram of cervical tissue.

EXAMPLE 6

Termination of pregnancy in the second trimester

Example 4 is repeated with the following modifications. The active substance and its method of administration and the dosage is as described in Example 5.

EXAMPLE 7

Termination of pregnancy in the second trimester

Example 5 is repeated with the following modifications. The active substance being Interleukin 2. The active substance and saline are administered extra-amniotically as a tablet, capsule or micro-capsule.

EXAMPLE 8

Termination of pregnancy in the second trimester

Example 5 is repeated with the following modifications. The active-substance being Interleukin 6. It is applied to the cervix as a tablet, capsule or micro-capsule form.

EXAMPLE 9

Termination of pregnancy in the second trimester

Example 4 is repeated with the following modifications. The active substance and its method of administration and the dosage is as in Example 8.

EXAMPLE 10

Termination of pregnancy in the second trimester

Example 8 is repeated with the following modifications. The active substance being Interleukin 8.

EXAMPLE 11

Termination of pregnancy in the second trimester

Example 4 is repeated with the following modifications. The active substance and its method of administration and the dosage is as in Example 10.

EXAMPLE 12

Termination of pregnancy in the second trimester

Example 5 is repeated with the following modification. The active substance is tumor necrosis factor. It is applied to the vagina in table, capsule or micro-capsule form.

EXAMPLE 13

Termination of pregnancy in the second trimester

Example 4 is repeated with the following modifications. The active substance and its method of administration and the dosage is as in Example 12.

EXAMPLE 14

Women before undergoing induction of labor in the third trimester

This may be necessary because of the mother's condition (e.g. hypertension, diabetes, etc.) or to induce labor post-term (42 completed weeks) or in term due to fetal causes (intra-uterine growth retardation (I.U.G.R.) or non-reactive non-stress test (N.S.T.), etc).

Fifty women undergoing induction of labor in the third trimester are used for this study. The same method as carried out in Example 1 above is applied.

EXAMPLE 15

Women before undergoing hysterectomy

Fifty women undergoing hysterectomy are used for this study. Collagenase and saline are injected 24 hours prior to hysterectomy in accordance with the method as described in Example 1 above. Cervical resistance is then be measured as described by Goldstuck. A hysterectomy specimen from each woman is semi-quantitatively histologically examined for collagen content and compared with the saline control group to ensure that there are no adverse side-effects and to measure the collagenase concentration in the blood.

The present invention thus provides for the use of collagenase and/or one or more substances which stimulate the production of naturally occurring collagen in obstetrics and gynecology to soften and ripen the cervix prior to termination of pregnancy or induction of labor in situations where the cervix is not in a favorable condition. Conventional procedures in which mechanical dilation of the cervix is effected by dilators with increasing diameters, can cause tearing or damage to the cervix. Induction of labor with prostaglandins locally and oxytocin intravenously can fail if the cervix is not in a favorable condition and may also be hazardous or toxic to the female if large doses are required. An advantage of using collagenase is that it comprises a naturally occurring enzyme that is physiologically compatible with the female's biochemistry and is generally non-toxic if used in prescribed dosages. The use of collagenase will facilitate induction of labor and termination of pregnancy and other procedures such as curettage, and is expected to minimize the incidence of caesarian sections which heretofore have needed to be performed. The use of collagenase is also expected to minimize or reduce damage to the uterine cervix caused during abortions using Hegar dilators, and to reduce cervix incompetence caused by any damage to the cervix during such operations.

I claim:

1. A method of softening or ripening the cervix of a female mammal, comprising administering a cervical-ripening amount of a collagenase to the cervix of said female mammal.

2. The method of claim 1 wherein said female mammal is human.

3. The method of claim 1 wherein the composition further comprises a substance selected from the group consisting of Interleukin 1 beta, Interleukin 6, Interleukin 8 and tumor necrosis factor.

4. A method of inducing labor in a female mammal, comprising administering a cervical-ripening amount of a collagenase to the cervix of said female mammal and thereafter an effective amount of a prostaglandin or oxytocin to said female mammal.

5. The method of claim 4 wherein said female mammal is human.

6. The method of claim 4 wherein the composition further comprises a substance selected from the group consisting of Interleukin 1 beta, Interleukin 6, Interleukin 8 and tumor necrosis factor.

7. A method of terminating pregnancy in a female mammal, comprising administering 1) a cervical-ripening amount of a collagenase to the cervix of said female mammal and thereafter 2) an effective amount of a prostaglandin or oxytocin to said female mammal.

8. The method of claim 7 wherein the composition further comprises a substance selected from the group consisting of Interleukin 1 beta, Interleukin 6, Interleukin 8 and tumor necrosis factor.

9. The method of claim 7 wherein said female mammal is human.

10. A method of ripening the cervix of a female mammal before diagnostic or operative procedures comprising administering a cervical-ripening amount of collagenase to the cervix of said female mammal.

11. The method of claim 10 further comprising administering a substance selected from the group consisting of Interleukin 1 beta, Interleukin 6, Interleukin 8 and tumor necrosis factor and combinations thereof.

12. The method of claim 10 wherein said female mammal is human.

13. The method of claim 1, wherein the amount of collagenase administered is an amount sufficient to provide a concentration in the range of from about 10 to about 200 I.U. per gram cervical tissue.

14. The method of claim 1, wherein the amount of collagenase administered is an amount sufficient to provide a concentration in the range of from about 10 to about 15 I.U. per gram cervical tissue.

15. The method of claim 4, wherein the amount of collagenase administered is an amount sufficient to provide a concentration in the range of from about 10 to about 200 I.U. per gram cervical tissue.

16. The method of claim 4, wherein the amount of collagenase administered is an amount sufficient to provide a concentration in the range of from about 10 to about 15 I.U. per gram cervical tissue.

17. The method of claim 7, wherein the amount of collagenase administered is an amount sufficient to provide a concentration in the range of from about 10 to about 200 I.U. per gram cervical tissue.

18. The method of claim 7, wherein the amount of collagenase administered is an amount sufficient to provide a concentration in the range of from about 10 to about 15 I.U. per gram cervical tissue.

19. The method of claim 10, wherein the amount of collagenase administered is an amount sufficient to provide a concentration in the range of from about 10 to about 200 I.U. per gram cervical tissue.

20. The method of claim 10, wherein the amount of collagenase administered is an amount sufficient to provide a concentration in the range of from about 10 to about 15 I.U. per gram cervical tissue.

21. The method of claim 10 wherein the collagenase is recombinant collagenase.

22. The method of claim 7, wherein said prostaglandin is $pgE_2\alpha$ or $pgF_2\alpha$ and said prostaglandin is administered extra-amniotically.

* * * * *